United States Patent
Moore, Jr. et al.

(10) Patent No.: US 6,495,169 B1
(45) Date of Patent: *Dec. 17, 2002

(54) CONCENTRATED AQUEOUS BROMINE SOLUTIONS AND THEIR PREPARATION

(75) Inventors: Robert M. Moore, Jr.; Christopher J. Nalepa, both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/456,781

(22) Filed: Dec. 8, 1999

Related U.S. Application Data

(63) Continuation of application No. 09/088,300, filed on Jun. 1, 1998, now Pat. No. 6,068,861.

(51) Int. Cl.[7] ........................ A01N 59/02; A01N 59/08; A01N 59/00
(52) U.S. Cl. ........................ 424/703; 424/663; 424/722; 424/723
(58) Field of Search ................................ 424/703, 723, 424/722, 663

(56) References Cited

U.S. PATENT DOCUMENTS

| | | | |
|---|---|---|---|
| 3,152,073 A | 10/1964 | Morton | 210/62 |
| 3,170,883 A | 2/1965 | Owen et al. | 252/187 |
| 3,308,062 A | 3/1967 | Gunther | 210/58 |
| 3,328,294 A | 6/1967 | Self et al. | 210/62 |
| 3,558,503 A | 1/1971 | Goodenough et al. | 252/187 |
| 3,589,859 A | 6/1971 | Foroulis | 21/2.7 |
| 3,711,246 A | 1/1973 | Foroulis | 21/2.7 |
| 3,749,672 A | 7/1973 | Golton et al. | 252/95 |
| 3,767,586 A | 10/1973 | Rutkiewic | 252/187 H |
| 4,032,460 A | 6/1977 | Zilch et al. | 252/8.55 B |
| 4,237,090 A | 12/1980 | DeMonbrun et al. | 422/13 |
| 4,295,932 A | 10/1981 | Pocius | 162/161 |
| 4,382,799 A | 5/1983 | Davis et al. | 8/107 |
| 4,427,435 A | 1/1984 | Lorenz et al. | 71/67 |
| 4,451,376 A | 5/1984 | Sharp | 210/701 |
| 4,465,598 A | 8/1984 | Darlington et al. | 210/721 |
| 4,476,930 A | 10/1984 | Watanabe | 166/279 |
| 4,490,308 A | 12/1984 | Fong et al. | 260/513 N |
| 4,539,071 A | 9/1985 | Clifford et al. | 162/161 |
| 4,546,156 A | 10/1985 | Fong et al. | 526/240 |
| 4,566,973 A | 1/1986 | Masler, III et al. | 210/701 |
| 4,595,517 A | 6/1986 | Abadi | 252/82 |
| 4,595,691 A | 6/1986 | LaMarre et al. | 514/367 |
| 4,604,431 A | 8/1986 | Fong et al. | 525/351 |
| 4,642,194 A | 2/1987 | Johnson | 210/699 |
| 4,643,835 A | 2/1987 | Koeplin-Gall et al. | 210/754 |
| 4,661,503 A | 4/1987 | Martin et al. | 517/372 |
| 4,680,339 A | 7/1987 | Fong | 525/54.11 |
| 4,680,399 A | 7/1987 | Buchardt | 546/139 |
| 4,703,092 A | 10/1987 | Fong | 525/351 |
| 4,711,724 A | 12/1987 | Johnson | 210/699 |
| 4,752,443 A | 6/1988 | Hoots et al. | 422/13 |
| 4,759,852 A | 7/1988 | Trulear | 210/699 |
| 4,762,894 A | 8/1988 | Fong et al. | 525/344 |
| 4,777,219 A | 10/1988 | Fong | 525/329.4 |
| 4,801,388 A | 1/1989 | Fong et al. | 210/701 |
| 4,802,990 A | 2/1989 | Inskeep, Jr. | 210/699 |
| 4,822,513 A * | 4/1989 | Corby | 252/106 |
| 4,846,979 A | 7/1989 | Hamilton | 210/754 |
| 4,883,600 A | 11/1989 | MacDonald et al. | 210/696 |
| 4,886,915 A | 12/1989 | Favstritsky | 564/503 |
| 4,898,686 A | 2/1990 | Johnson et al. | 252/389.2 |
| 4,906,651 A | 3/1990 | Hsu | 514/372 |
| 4,923,634 A | 5/1990 | Hoots et al. | 252/389.2 |
| 4,929,424 A | 5/1990 | Meier et al. | 422/9 |
| 4,929,425 A | 5/1990 | Hoots et al. | 422/13 |
| 4,966,716 A | 10/1990 | Favstritsky et al. | 210/755 |
| 4,992,209 A | 2/1991 | Smyk et al. | 252/387 |
| 4,995,987 A | 2/1991 | Whitekettle et al. | 210/754 |
| 5,034,155 A | 7/1991 | Soeder et al. | 252/389.23 |
| 5,035,806 A | 7/1991 | Fong et al. | 210/701 |
| 5,047,164 A | 9/1991 | Corby | 252/106 |
| 5,055,285 A | 10/1991 | Duncan et al. | 423/473 |
| 5,118,426 A | 6/1992 | Duncan et al. | 210/721 |

(List continued on next page.)

FOREIGN PATENT DOCUMENTS

| | | |
|---|---|---|
| WO | 9015780 | 12/1990 |
| WO | 9720546 | 6/1997 |
| WO | 9720909 | 6/1997 |
| WO | 9734827 | 9/1997 |
| WO | 9743392 | 11/1997 |
| WO | 9815609 | 4/1998 |
| WO | 9906320 | 2/1999 |
| WO | 9932596 | 7/1999 |
| WO | 9955627 | 11/1999 |

OTHER PUBLICATIONS

Willard et al., "Elementary Quantitative Analysis", Third Edition, Chaper XIV –Oxidation and Reduction Processes Involving Iodine (Iodometry) 1940, pp. 261–271.

Ault et al., "Infrared and Raman Spectra of the $M^+Cl_3^-$ ion Pairs and Their Chlorine–bromine Counterparts isolated in Argon Matrices", Journal of Chemical Physics, 1976, vol. 64, No. 12, pp. 4853–4859.

*Primary Examiner*—Alton Pryor
(74) *Attorney, Agent, or Firm*—Edgar E. Spielman, Jr.

(57) ABSTRACT

Described is a process of producing a concentrated liquid biocide formulation. Mixed together are (a) bromine chloride or bromine and (b) an aqueous solution of alkali metal salt of sulfamic acid having a pH of at least about 7, in amounts such that (i) the active bromine content of the solution is at least about 100,000 ppm (wt/wt), and (ii) the atom ratio of nitrogen to active bromine from (a) and (b) is greater than 1 when bromine is used and is greater than 0.93 when bromine chloride is used. Use of bromine chloride as the source of the active bromine in the process is preferred because in the resulting aqueous compositions, all of the bromine of the bromine chloride is made available as active bromine in solution. In other words, the chlorine of the bromine chloride is converted in the process to dissolved alkali metal chloride salt, thereby liberating all of the bromine as the active bromine content of the biocidal composition.

8 Claims, No Drawings

U.S. PATENT DOCUMENTS

| | | | |
|---|---|---|---|
| 5,120,452 A | 6/1992 | Ness et al. | 210/754 |
| 5,120,797 A | 6/1992 | Fong et al. | 525/329.4 |
| 5,141,652 A | 8/1992 | Moore, Jr. et al. | 210/754 |
| 5,179,173 A | 1/1993 | Fong et al. | 525/329.4 |
| 5,192,459 A | 3/1993 | Tell et al. | 252/106 |
| 5,194,238 A | 3/1993 | Duncan et al. | 423/473 |
| 5,196,126 A | 3/1993 | O'Dowd | 210/754 |
| 5,202,047 A | 4/1993 | Corby | 252/106 |
| 5,259,985 A | 11/1993 | Nakanishi et al. | 252/180 |
| 5,264,136 A | 11/1993 | Howarth et al. | 210/754 |
| 5,389,384 A | 2/1995 | Jooste | 424/661 |
| 5,414,652 A | 5/1995 | Mieda et al. | 365/122 |
| 5,424,032 A | 6/1995 | Christensen et al. | 422/14 |
| 5,443,849 A | 8/1995 | Corby | 424/667 |
| 5,464,636 A | 11/1995 | Hight et al. | 424/661 |
| 5,525,241 A | 6/1996 | Clavin et al. | 210/753 |
| 5,527,547 A | 6/1996 | Hight et al. | 424/661 |
| 5,589,106 A | 12/1996 | Shim et al. | 252/387 |
| 5,607,619 A | 3/1997 | Dadgar et al. | 252/187.2 |
| 5,679,239 A | 10/1997 | Blum et al. | 205/556 |
| 5,683,654 A | 11/1997 | Dallmier et al. | 422/14 |
| 5,795,487 A | 8/1998 | Dallmier et al. | 210/754 |
| 5,900,512 A | 5/1999 | Elnagar et al. | 568/14 |
| 5,922,745 A | 7/1999 | McCarthy et al. | 514/372 |
| 5,942,126 A | 8/1999 | Dallmier et al. | 210/752 |
| 6,007,726 A | 12/1999 | Yang et al. | 210/752 |
| 6,068,861 A * | 5/2000 | Moore, Jr. et al. | 424/703 |
| 6,123,870 A | 9/2000 | Yang et al. | 252/186.1 |
| 6,156,229 A | 12/2000 | Yang et al. | 252/186.1 |

* cited by examiner

CONCENTRATED AQUEOUS BROMINE SOLUTIONS AND THEIR PREPARATION

REFERENCE TO RELATED APPLICATIONS

This is a continuation of commonly-owned Continued Prosecution Application (CPA) No. 09/088,300 now issued as U.S. Pat. No. 6,068,861, filed Jun. 1, 1998 which continues the prosecution of commonly-owned copending Application Ser. No. 09/088,300, filed Jun. 1, 1998.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to HOBr/OBr$^\ominus$. This a activated solution is then introduced directly into the water system to be treated. The feeding of the two liquids in this fashion is necessary because the HOBr/OBr$^\ominus$ mixture is unstable and has to be generated on-site just prior to its introduction to the water. Furthermore, the feeding, and metering of two liquids is cumbersome, especially as the system has to be designed to allow time for the activation of bromide ion to occur. Consequently many biocide users have expressed the need for a single-feed, bromine-based biocide. Elemental bromine and molecular bromine chloride have been considered to meet these demands. Both are liquids at room temperature and can be fed directly to the water system, where immediate hydrolysis occurs to yield HOBr.

$$Br_2+H_2O \rightarrow HOBr+HBr \quad (1)$$

$$BrCl+H_2O \rightarrow HOBr+HCl \quad (2)$$

Properties of bromine and bromine chloride are compared in Table 1.

TABLE 1

Physical Properties of Bromine and Bromine Chloride

| Property | Bromine (Br$_2$) | Bromine Chloride (BrCl) |
|---|---|---|
| Appearance | Fuming, dark-red liquid | Fuming, red liquid or gas |
| Boiling Point | 59° C. | 5° C. |
| Vapor Pressure (25° C.) | 214 mm | 1800 mm |
| Corrosivity | Corrodes most metals in the presence of water | Corrodes most metals in the presence of water |

It can be seen that certain characteristics of these materials—especially their corrosiveness, high vapor pressures and fuming tendencies—necessitate care and skill in their handling and use. Early efforts to overcome the deficiencies of these materials comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Favstritsky, U.S. Pat. No. 4,886,915; and Favstritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine derivatives such as BCDMH (1,3-bromochloro-5,5-dimethylhydantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallhmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

THE INVENTION

This invention involves a new process of forming concentrated aqueous solutions of biocidally active bromine and in so doing, provides novel and eminently useful concentrated aqueous biocidal solutions of bromine and bromine chloride.

In one of its embodiments this invention provides a process of producing a concentrated liquid biocide composition which comprises mixing (a) bromine chloride or bromine with (b) an aqueous solution of alkali metal salt of sulfamic acid (preferably the sodium salt), the solution having a pH of at least about 7, e.g., in the range of 7 to about 13.5, and preferably in the range of 7 to about 12. The amounts of (a) and (b) used are such that (i) the content of active bromine in the solution is at least 100,000 ppm (wt/wt) and (ii) the atom ratio of nitrogen to active bromine from (a) and (b) is greater than 1 when bromine is used, and greater than 0.93 when bromine chloride is used. It is preferred, however, to utilize an atom ratio of nitrogen to active bromine from (a) and (b) that is greater than 1 even when using bromine chloride in the process. In a preferred embodiment the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 7. If sulfamic acid itself is used as the starting material, it is used initially as a slurry in water with which the alkali metal base is mixed.

When introducing the bromine chloride or bromine into the aqueous solution of alkali metal salt of sulfamic acid, it is desirable to maintain the desired pH of the resulting solution at 7 or above by also introducing into the solution (continuously or intermittently, as desired) additional alkali metal base, such as by a co-feed of an aqueous solution of alkali metal base.

It is preferred to employ bromine chloride as the source of the active bromine in the above process because in the resulting aqueous compositions, all of the bromine of the bromine chloride is made available as active bromine in solution. In other words, the chlorine of the bromine chloride is converted in the process to dissolved alkali metal chloride salt, thereby liberating the bromine as the active bromine content of the biocidal composition. Thus the more expensive component of the bromine chloride—viz., bromine—is fully utilized in forming active bromine in the aqueous biocidal composition, and concurrently the less expensive component—the anionic chlorine in the bromine chloride—makes this beneficial result possible.

By utilizing bromine or bromine chloride with caustic in the stabilized bromine composition, higher levels of active halogen are achievable, compared to the levels obtained by the addition of sodium hypochlorite to sodium bromide. The process and the compositions formed also have about twice the content of active bromine as the most concentrated solutions produced pursuant to the Goodenough, et al. patent. Moreover, even at the high levels of active bromine that exist in the compositions of this invention, it has been found possible to provide biocidal compositions that maintain these high levels of active bromine for at least a two-month period, and that do not exhibit a visible or offensive vapor or odor during this period.

In another embodiment, alkali metal dichlorohypobromite, M[BrCl$_2$] (M=alkali metal) is preformed by pre-mixing bromine chloride with aqueous sodium chloride, and the bromine chloride is used in this form to provide the active bromine content of the resultant solution. The preferred alkali metal dichlorohypobromite is sodium dichlorohypobromite.

Another embodiment of this invention is an aqueous biocide composition comprising water having in solution therein (i) an active bromine content derived from bromine chloride of at least about 100,000 ppm (wt/wt), (ii) an alkali metal salt of sulfamic acid (preferably the sodium salt), and (iii) an alkali metal chloride (preferably sodium chloride), wherein the relative proportions of (i) and (ii) are such that the atom ratio of nitrogen to active bromine is greater than 1, and wherein the pH of the composition is at least 7, e.g., in the range of 7 to about 13.5, and preferably in the range of 7 to about 12. In a less preferred embodiment (i) is bromine (Br$_2$) and (iii) is an alkali metal bromide (especially sodium bromide).

In each of the embodiments of this invention, the atom ratio of nitrogen to active bromine is preferably in the range of about 1.1 to about 1.5. Still higher ratios can be employed, if desired.

The above and other embodiments of this invention will be still further apparent from the ensuing description and appended claims.

A general procedure for preparing the compositions of this invention using sulfamic acid involves, as a first step, forming a slurry of sulfamic acid in water. Typically the pH of this slurry is below 1 pH unit. Sodium hydroxide at 50% concentration is then added until the solid is completely dissolved. Additional 50% NaOH is added until the desired pH is reached. Bromine or bromine chloride is then added at a rate to allow the bromine to dissolve and react with the sulfamic acid without forming a pool of halogen on the bottom of the reactor. On a laboratory scale, a convenient rate of addition is approximately two drops per second. Sodium hydroxide (e.g., 25% or 50%) is co-fed to the reactor to maintain the desired pH (e.g., in the range of 7 to about 13.5, and it may be possible to operate even at a pH in the range of 13.5 to 14. It has been found that stable solutions containing as much as 26% active bromine (11.5% on an active chlorine basis) can be prepared by the process of this invention.

The following examples are presented for purposes of illustration and not limitation.

EXAMPLES

Various compositions were prepared using the above general procedure and the active bromine content of the resultant compositions was determined analytically. The conditions used and results obtained (observations on odor and vapor, and initial contents of active bromine in the solutions) are summarized in Table 2.

TABLE 2

Data on Prepared Sulfamic Acid Stabilized Bromine Solutions

| Ex. No. | Halogen | pH | SA$_{eq}$ | Odor and Vapor Comments | Active Br$_2$, wt % |
|---|---|---|---|---|---|
| 1 | Br$_2$ | 13.0 | 1.42 | Slight sweet smell, no observed vapor | 12.4%* |
| 2 | Br$_2$ | 7.0 | 1.48 | Slight Br odor, no fuming | 13.4%* |
| 3** | BrCl | 7 | 0.92 | Strong Br odor, slight fuming | 11.2% |
| 4 | Br$_2$ | 13.0 | 1.15 | Slight sweet smell, no observed vapor | 19.6% |
| 5 | Br$_2$ | 7.0 | 1.13 | Moderate Br odor, no fuming | 26.7% |
| 6 | BrCl | 12.5 | 0.94 | Slight sweet smell, no observed vapor | 18.0% |
| 7 | BrCl | 12.8 | 1.41 | Slight sweet smell, no observed vapor | 17.6% |

SA$_{eq}$ = Sulfamic acid to halogen mole ratio.
*Measured with Hach spectrometer; all others titrated using starch-iodine-sodium arsenite method.
**Comparative example.

The specific details for Examples 3-7 of the Table are given below. Example 8 illustrates the embodiment of the invention wherein an alkali metal dichlorohypobromite is utilized as the source of active bromine.

Example 3
Bromine Chloride, Caustic and Sodium Sulfamate at Neutral pH

A 1 liter flask was charged with 52.0 g of sulfamic acid and 250 g of water. Sodium sulfamate was prepared by adding 60.0 g of 50% sodium hydroxide to the stirred slurry. Bromine chloride was prepared by adding 20 g of chlorine to 47.0 g of bromine. This bromine chloride was then co-fed with 210 g of 25% sodium hydroxide to maintain the pH between 6 and 8.5 mL of 1 M Hydrochloric Acid were added to bring the final pH to approximately 7±0.5. The solution, which contained some solids, was transferred to an amber bottle for storage. Starch-iodine titration of a sample of the solution indicated that it had an active bromine concentration of 11.2%.

Example 4
Bromine, Caustic (50% Sodium Hydroxide) and Sodium Sulfamate

A 500 mL flask was charged with 26.0 g of sulfamic acid and 50 g water. To this slurry was added 35.0 g of 50% sodium hydroxide. As the acid was converted to the sodium salt, it dissolved into the aqueous solution more readily. Bromine (37.0 g) and 50% sodium hydroxide (30.0 g) were co-fed into the solution at a rate which maintained the pH between 11 and 13. After all of the bromine and caustic had been added, the contents were transferred to an amber bottle for storage. Starch-iodine titration of a sample of the solution indicated that it had an active bromine concentration of 19.6%. Analysis of the bromine solution still contained more than 95% of its active bromine content.

Example 5
Bromine, Caustic and Sodium Sulfamate at Neutral pH

A 500 mL flask was charged with 26.0 g of sulfamic acid and 50 g of water. To this stirred slurry was added 30.9 g of 50% sodium hydroxide, which raised the initial pH to approximately 12. The sulfamic acid then dissolved into solution. Bromine (37.7 g) was fed into the solution until the pH dropped to approximately 7, when 50% sodium hydroxide (10.9 g) was co-fed to maintain the pH between 6 and 9.5 ML of 0.01 N sodium hydroxide was used to bring the final pH to approximately 7±0.5. The contents were then transferred to an amber bottle for storage. Starch-iodine titration of a sample of this solution indicated that it had an active bromine content of 26.7%. Analysis of the solution after six weeks of storage at ambient temperature indicated that the stabilized bromine solution still contained more than 95% of its active bromine content.

Example 6
Bromine Chloride, Caustic and Sodium Sulfamate

A 1 liter flask was charged with 107 g of sulfamic acid and 200 g of water. Sodium sulfamate was prepared by adding 93.9 g of 50% sodium hydroxide to the stirred slurry. Bromine chloride was prepared by adding 39 g of chlorine to 96.0 g of bromine. This bromine chloride was the co-fed with 319 g of 50% sodium hydroxide to maintain the pH between 11 and 13. After stirring for an additional 30 minutes, the solution, which contained some solids, was transferred to an amber bottle for storage. Starch-iodine titration of a sample of the solution indicated that it had an active bromine concentration of 18.0%. Analysis of the solution after three weeks at ambient temperature indicated that the stabilized bromine solution still contained more than 90% of its active bromine content.

Example 7
Bromine Chloride, Caustic and Sodium Sulfamate; Larger Scale

A 5 liter flask was charged with 470 g of sulfamic acid and 900 g of water. Sodium sulfamate was prepared by adding 436 g of 50% sodium hydroxide to the stirred slurry.

Bromine chloride was prepared by adding 120 g of chlorine to 276 g of bromine. This bromine chloride was the co-fed with 1723 g of 50% sodium hydroxide to maintain the pH between 12 and 13. After stirring for an additional 60 minutes, the orange, clear solution was transferred to an polyethylene bottle for storage. Starch-iodine titration of a sample of the solution indicated that it had an active bromine concentration of 17.6%.

Example 8
Reducing Vapor Pressure of Sodium Dichlorohypobromite with Sodium Sulfamate Sodium sulfamate was prepared by slurrying 24.3 g of sulfamic acid in 9 g of water. 24.0 g of 50% sodium hydroxide was added dropwise. The flask heated noticeably and the solid dissolved. This solution was dropped into 184.6 g of sodium dichlorohypobromite. Sodium dichlorohypobromite, $Na[BrCl_2]$ is prepared by adding 30.6 g of bromine chloride to 154 g of 3M aqueous sodium chloride. An additional 24 g of 50% sodium hydroxide was added to raise the pH to 7. Analysis of this solution indicated that it had an active bromine concentration of 12.0%.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing a concentrated liquid biocide formulation which comprises mixing together compounds/liquids consisting essentially of (a) bromine chloride and (b) an aqueous solution of alkali metal salt of sulfamic acid having a pH of at least 7, and alkali metal hydroxide in amounts such that (i) the active bromine content of the formulation is at least about 100,000 ppm (wt/wt), and (ii) the atom ratio of nitrogen to active bromine from (a) and (b) is in the range of about 1.1 to about 1.5 the amount of alkali being at least sufficient to have the pH of the formulation at a pH of at least 7.

2. A process according to claim 1 wherein said aqueous solution of alkali metal salt of sulfamic acid is an aqueous solution of sodium sulfamate.

3. A process according to claim 1 or 2 wherein the bromine chloride is formed from chlorine and bromine in a chlorine:bromine weight ratio in the range of about 1.0:2.3 to about 1.0:2.5.

4. A process of producing a concentrated liquid biocide formulation which comprises co-feeding compounds/liquids consisting essentially of (a) bromine chloride and (b) an aqueous solution of alkali metal hydroxide into an aqueous solution of alkali metal sulfamate in amounts such that (i) an active bromine content of the formulation solution is at least about 100,000 ppm (wt/wt), (ii) the atom ratio of nitrogen to active bromine from (a) and (b) in the formulation solution is greater than 0.93, the amount of the alkali metal hydroxide being at least sufficient to have the pH of the formulation at least at 7.

5. A process according to claim 4 wherein said aqueous solution of alkali metal hydroxide is a 25 wt % solution of sodium hydroxide, and wherein the pH of the formulation being formed is maintained between 7 and 8 during said co-feeding.

6. A process according to claim 4 wherein said aqueous solution of alkali metal hydroxide is a 50 wt % solution of sodium hydroxide, and wherein the pH of the formulation being formed is maintained between 11 and 13 during said co-feeding.

7. A process according to claim 4 wherein said aqueous solution of alkali metal hydroxide is a 50 wt % solution of sodium hydroxide, and wherein the pH of the formulation being formed is maintained between 12 and 13 during said co-feeding.

8. A process according to claim 4 wherein said atom ratio of nitrogen to active bromine from (a) and (b) is in the range of about 1.1 to about 1.5.

* * * * *